United States Patent
Baker

(10) Patent No.: US 10,357,626 B1
(45) Date of Patent: Jul. 23, 2019

(54) LINER FOR A RESPIRATOR MASK

(71) Applicant: Bruce O. Baker, Big Rapids, MI (US)

(72) Inventor: Bruce O. Baker, Big Rapids, MI (US)

(*) Notice: Subject to any disclaimer, the term of this patent is extended or adjusted under 35 U.S.C. 154(b) by 898 days.

(21) Appl. No.: 14/317,667

(22) Filed: Jun. 27, 2014

Related U.S. Application Data

(60) Provisional application No. 61/857,453, filed on Jul. 23, 2013.

(51) Int. Cl.
*A61M 16/06* (2006.01)
*A61M 16/10* (2006.01)
*A61M 16/00* (2006.01)

(52) U.S. Cl.
CPC .... *A61M 16/0622* (2014.02); *A61M 16/0057* (2013.01); *A61M 16/105* (2013.01); *A61M 2016/0661* (2013.01)

(58) Field of Classification Search
CPC .............. A61M 16/06; A61M 16/0605; A61M 16/0688; A61M 16/0622; A61M 16/0615; A62B 18/08; A41D 13/1176; A41D 13/1161; A41D 13/1169; A41D 2500/20
See application file for complete search history.

(56) References Cited

U.S. PATENT DOCUMENTS

| | | | |
|---|---|---|---|
| 1,990,199 A | 2/1935 | Nemzek | |
| 2,008,677 A | 7/1935 | Booharin | |
| 2,237,305 A * | 4/1941 | Heimann | A41D 13/1161 128/206.13 |
| 2,435,721 A | 2/1948 | Lehmann | |
| 2,931,356 A | 4/1960 | Schwarz | |
| 3,130,722 A | 4/1964 | Dempsey et al. | |
| 4,069,516 A | 1/1978 | Watkins, Jr. | |
| D257,063 S | 9/1980 | Galindo | |
| 4,856,508 A | 8/1989 | Tayebi | |

(Continued)

FOREIGN PATENT DOCUMENTS

| | | |
|---|---|---|
| CN | 1681551 | 10/2005 |
| CN | 1681553 | 10/2005 |

(Continued)

OTHER PUBLICATIONS

"Mirage Micro Nasal Mask", ResMed, 2007, from www.resmed.com.

(Continued)

*Primary Examiner* — Gregory A Anderson
*Assistant Examiner* — Margaret M Luarca
(74) *Attorney, Agent, or Firm* — Brooks Kushman P.C.

(57) ABSTRACT

A respirator mask liner is provided for positioning between a respirator mask and the face of a wearer. The mask liner includes a flexible sheet material having an outer perimeter edge portion and a hole that is spaced inwardly from the outer perimeter edge portion. At least one tab projects outwardly from portions of the perimeter edge portion, and may be unitarily formed with the sheet material. The mask liner is configured so that when it is to be placed between the face of the wearer and the respirator mask, the tab or tabs project outwardly beyond the gasket portion of the respirator mask, so that the tabs may be used for adjusting the liner or securing the liner to the mask. Optionally, the mask liner has a surface texture with a ribbed and undulating pattern of raised portions, and/or incorporates an anti-microbial substance.

19 Claims, 6 Drawing Sheets

(56) References Cited

U.S. PATENT DOCUMENTS

| | | | |
|---|---|---|---|
| 5,003,633 | A | 4/1991 | Itoh |
| 5,921,239 | A | 7/1999 | McCall et al. |
| 6,016,805 | A | 1/2000 | Burns et al. |
| 6,082,360 | A | 7/2000 | Rudolph et al. |
| 6,196,223 | B1 | 3/2001 | Belfer et al. |
| D442,352 | S | 5/2001 | Benjamin et al. |
| 6,338,340 | B1 | 1/2002 | Finch et al. |
| 6,468,222 | B1 | 10/2002 | Mault et al. |
| 6,629,531 | B2 | 10/2003 | Gleason et al. |
| 6,698,427 | B1 | 3/2004 | Clowers |
| 6,698,727 | B1 | 3/2004 | Clowers |
| 6,851,429 | B2 | 2/2005 | Bishop |
| 6,926,004 | B2 | 8/2005 | Schumacher |
| 6,955,650 | B2 | 10/2005 | Mault et al. |
| 7,000,614 | B2 | 2/2006 | Lang et al. |
| 7,017,577 | B2 | 3/2006 | Matich |
| 7,077,138 | B2 | 7/2006 | Bateman et al. |
| 7,178,525 | B2 | 2/2007 | Matula, Jr. et al. |
| 7,219,670 | B2 | 5/2007 | Jones, Jr. et al. |
| 7,243,650 | B2 | 7/2007 | Thornton |
| 7,296,574 | B2 | 11/2007 | Ho et al. |
| 7,370,652 | B2 | 5/2008 | Matula, Jr. et al. |
| 7,472,703 | B2 | 1/2009 | Hernandez et al. |
| D644,729 | S | 9/2011 | Ferris et al. |
| 8,171,934 | B1 | 5/2012 | Ho |
| 8,365,733 | B2 | 2/2013 | Rutan |
| D717,939 | S | 11/2014 | Koehler |
| D735,318 | S | 7/2015 | Roblin-Lee |
| 9,113,667 | B2 | 8/2015 | Rutan |
| D738,514 | S | 9/2015 | Tagami et al. |
| D755,951 | S | 5/2016 | Roblin-Sharp |
| 2003/0023182 | A1 | 1/2003 | Mault et al. |
| 2004/0194784 | A1* | 10/2004 | Bertrand .......... A62B 23/06 128/206.18 |
| 2004/0244799 | A1 | 12/2004 | Landis |
| 2004/0244804 | A1 | 12/2004 | Olsen et al. |
| 2004/0261797 | A1 | 12/2004 | White et al. |
| 2005/0199239 | A1 | 9/2005 | Lang et al. |
| 2005/0279367 | A1 | 12/2005 | Klemperer |
| 2005/0284481 | A1 | 12/2005 | Meyer et al. |
| 2006/0107431 | A1 | 5/2006 | Curran et al. |
| 2006/0144399 | A1 | 7/2006 | Davidowski et al. |
| 2006/0283452 | A1 | 12/2006 | Woodard et al. |
| 2007/0006879 | A1 | 1/2007 | Thornton |
| 2007/0050883 | A1 | 3/2007 | Matich |
| 2007/0175479 | A1 | 8/2007 | Groll |
| 2007/0175480 | A1 | 8/2007 | Gradon et al. |
| 2008/0047560 | A1 | 2/2008 | Veliss et al. |
| 2008/0110469 | A1 | 5/2008 | Weinberg |
| 2008/0127984 | A1 | 6/2008 | Thornton |
| 2008/0257354 | A1 | 10/2008 | Davidson et al. |
| 2008/0302365 | A1 | 12/2008 | Cohen et al. |
| 2009/0050144 | A1 | 2/2009 | Pierce et al. |
| 2009/0107507 | A1 | 4/2009 | Moore |
| 2009/0139525 | A1 | 6/2009 | Schirm |
| 2009/0211581 | A1 | 8/2009 | Bansal |
| 2009/0293880 | A1 | 12/2009 | Rutan |
| 2010/0031958 | A1 | 2/2010 | Stewart |
| 2010/0326445 | A1 | 12/2010 | Veliss et al. |
| 2011/0005524 | A1* | 1/2011 | Veliss .......... A61M 16/0666 128/206.24 |
| 2011/0061656 | A1 | 3/2011 | Matich |
| 2011/0226240 | A1 | 9/2011 | Navalesi et al. |
| 2012/0180795 | A1 | 7/2012 | Knight |
| 2012/0204881 | A1* | 8/2012 | Davidson .......... A61M 16/06 128/206.25 |
| 2013/0139290 | A1* | 6/2013 | Barski .......... A41B 13/06 2/69.5 |
| 2013/0139829 | A1 | 6/2013 | Rutan |
| 2014/0150799 | A1 | 6/2014 | Daly |
| 2014/0190492 | A1 | 7/2014 | Noh et al. |
| 2015/0352307 | A1 | 12/2015 | Rutan |
| 2015/0352309 | A1 | 12/2015 | Daly |
| 2015/0374943 | A1 | 12/2015 | Alexani |
| 2015/0374945 | A1 | 12/2015 | Anthony |
| 2016/0279359 | A1 | 9/2016 | Chang et al. |
| 2016/0339196 | A1 | 11/2016 | Bowsher |
| 2017/0049983 | A1 | 2/2017 | Ellis |

FOREIGN PATENT DOCUMENTS

| | | |
|---|---|---|
| JP | S44-20956 | 9/1969 |
| JP | 2-42295 | 11/1990 |
| JP | 2000-217940 | 8/2000 |
| JP | 2003052845 | 2/2003 |
| WO | 1999/25410 | 5/1999 |
| WO | 2000/50121 | 8/2000 |
| WO | 00/76568 | 12/2000 |
| WO | 2004/022145 | 3/2004 |
| WO | 2008/011683 | 1/2008 |

OTHER PUBLICATIONS (2006), CPAP Community—View Topic—Mask Gasket [Web log post]. Retrieved from http://www.cpaptalk.com/viewtopic.

(2006), CPAP Community—View Topic—Mask Experiment Success [Web log post]. Retrieved from http://www.cpaptalk.com/viewtopic.

(2005), CPAP Community—View Topic—Directions for Toilet Seat Covering [Web log post]. Retrieved from http://www.cpaptalk.com/viewtopic.

(2005-2011), CPAP Community—View Topic—Directions for Toilet Seat Covering [Web log post]. Retrieved from http://www.cpaptalk.com/viewtopic.

"Pad a Cheek", PAC_OptiLife, from http://www.padacheek.com/PAC_Maskliner.html, obtained from www.archive.org, published at least as early as Apr. 8, 2012.

(Nov. 22, 2007), CPAP Community, "Deconstructed Aura" [Web log post]. Retrieved from http://www.cpaptalk.com/viewtopic.

(2007), CPAP Community [Web log post]. Retrieved from http://www.cpaptalk.com/viewtopic.

(Nov. 30, 2007), CPAP Community, "what is wrong with me" [Web log post]. Retrieved from http://www.cpaptalk.com/viewtopic.

(Dec. 12, 2008), CPAP Community, "Any one tried a mask cover-gasket" [Web log post]. Retrieved from http://www.cpaptalk.com/viewtopic.

(2005), CPAP Community [Web log post]. Retrieved from http://www.cpaptalk.com/viewtopic.

* cited by examiner

LINER FOR A RESPIRATOR MASK

CROSS REFERENCE TO RELATED APPLICATION

The present application claims the benefit of U.S. provisional application Ser. No. 61/857,453, filed Jul. 23, 2013, which is hereby incorporated herein by reference in its entirety.

FIELD OF THE INVENTION

The present invention relates generally to respirator masks and, more particularly, to liners placed between a respirator mask, such as a CPAP mask, and a wearer's face.

BACKGROUND OF THE INVENTION

Many types of respirators are available for different uses, such as air filtration, or for providing clean air or breathing gases at positive supply pressure to persons in hazardous breathing environments, such as firefighters and soldiers, or for cleanroom workers, medical patients, sleep apnea sufferers, etc. Many such respirators include a flexible mask portion that engages and at least partially conforms to portions of a wearer's face, surrounding the nose and/or mouth. The mask portion is typically made at least partially from a flexible rubber or rubber-like material, such as silicone.

SUMMARY OF THE INVENTION

The present invention provides a flexible liner that is placed between the nose and/or mouth of a wearer, and a respirator mask. Tabs or projections extend outwardly from the liner and facilitate alignment and positioning of the liner relative to the respirator mask, while also providing the wearer with grasping surfaces to facilitate adjustment of the liner. The tabs allow for adjustment of the liner even with the respirator mask remaining in position at the wearer's face. The liner increases wearer comfort by providing moisture-wicking, improved sealing (i.e., reducing air leaks), and allowing for reduced mask pressure. The liner may also be washable and reusable, and may include an anti-microbial and/or anti-bacterial substance. The liner may be made from a medium-weight fabric, such as a cotton/synthetic blend, which is sufficiently flexible to conform to both the mask and the wearer's face, while resisting undesirable wrinkling or curling at the edges.

In one form of the present invention, the respirator mask liner is made up of a flexible sheet material having an outer perimeter edge portion, with a hole or opening that is formed or established in a central region of the sheet, spaced inwardly from the outer perimeter edge portion. The sheet includes at least one tab or tab portion that projects outwardly from adjacent portions of the perimeter edge portion. The flexible sheet material is configured to be placed between the face of a wearer and a gasket portion of a respirator mask, so that the tab projects outwardly beyond the gasket portion of the respirator mask.

Optionally, the respirator mask liner has a skin-contacting surface with a ribbed and undulating pattern that obstructs airflow between the skin-contacting surface and the wearer's skin. For example, the skin-contacting surface may define a plurality of raised portions in spaced arrangement. The raised portions can be arranged at an interval of about 2-3 mm in a first direction and at an interval of about 5-7 mm in a second direction that is substantially perpendicular to the first direction.

Optionally, the respirator mask liner incorporates an anti-microbial substance that substantially inhibits the growth of bacteria or microbes on the liner. The anti-microbial substance may be incorporated at the flexible sheet portion by anti-microbial spray application, an anti-microbial bath dip, or incorporation of anti-microbial fibers woven into the material.

Thus, the present invention provides a flexible liner that enhances both wearer comfort and functionality of a respirator mask. The liner may have moisture-wicking properties, and is flexible to conform to both the wearer's face and the respirator mask. The liner may be attached directly to the respirator mask, and/or may remain repositionable to ensure a comfortable and well-sealing fit. In addition, the liner may have a surface texture that includes very small or microscopic ridges, baffles, or repeating pillow-like texture, that enhance the air-sealing qualities and comfort of the mask-to-wearer interface.

These and other objects, advantages, purposes and features of the present invention will become apparent upon review of the following specification in conjunction with the drawings.

DESCRIPTION OF THE PREFERRED EMBODIMENTS

Figure 1:
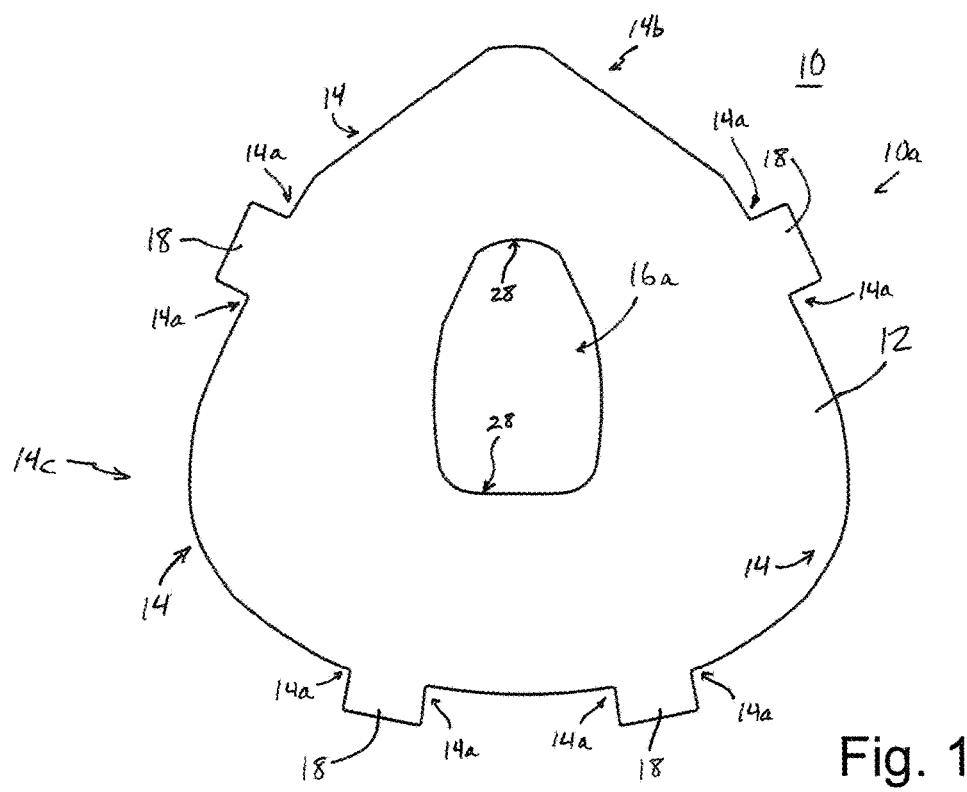
FIG. 1 is a top plan view of a respirator mask liner in accordance with the present invention.

Referring now to the drawings and the illustrative embodiments depicted therein, a flexible liner is provided for wearing between a respirator mask and the nose and/or mouth of a wearer, which enhances both wearer comfort and functionality of the mask. In the illustrated embodiment of FIGS. 1-3, three different mask liners 10a-c (which may be designated generally with reference numeral 10) have somewhat different shapes or configurations, but are otherwise substantially similar to one another in function, as will be described below. Each liner 10 is made from a flexible sheet material 12 having an outer perimeter edge portion 14. Each sheet 12 defines a hole or opening 16 that is spaced inwardly from the outer perimeter edge portion 14, and which receives a portion of the wearer's nose and/or mouth. A plurality of tabs 18 project outwardly from respective portions 14a of the perimeter edge portion 14 that are adjacent the tabs 18. The flexible sheet 12, which is typically made of fabric as described below, may be placed between the face 20 of a wearer 22 and a face engaging gasket, cushion, or seal portion 24*a* of a respirator mask 24, such as shown in FIG. 4, with the tab or tabs 18 projecting outwardly beyond the gasket portion 24*a* of the respirator mask 24.

Figure 2:
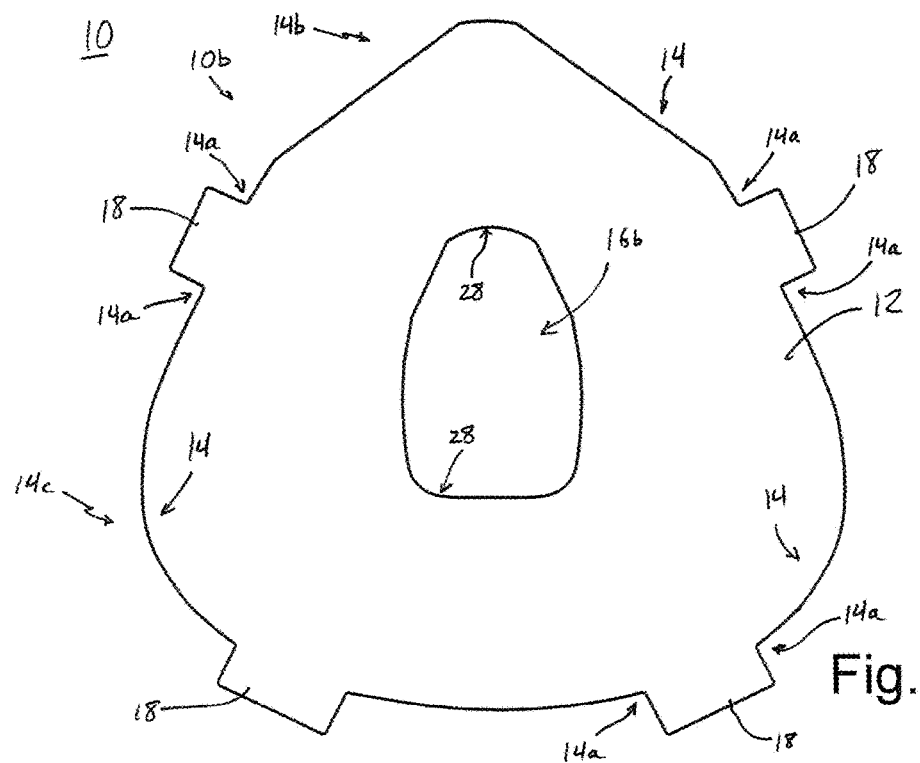
FIG. 2 is a top plan view of another respirator mask liner in accordance with the present invention.
Figure 3:
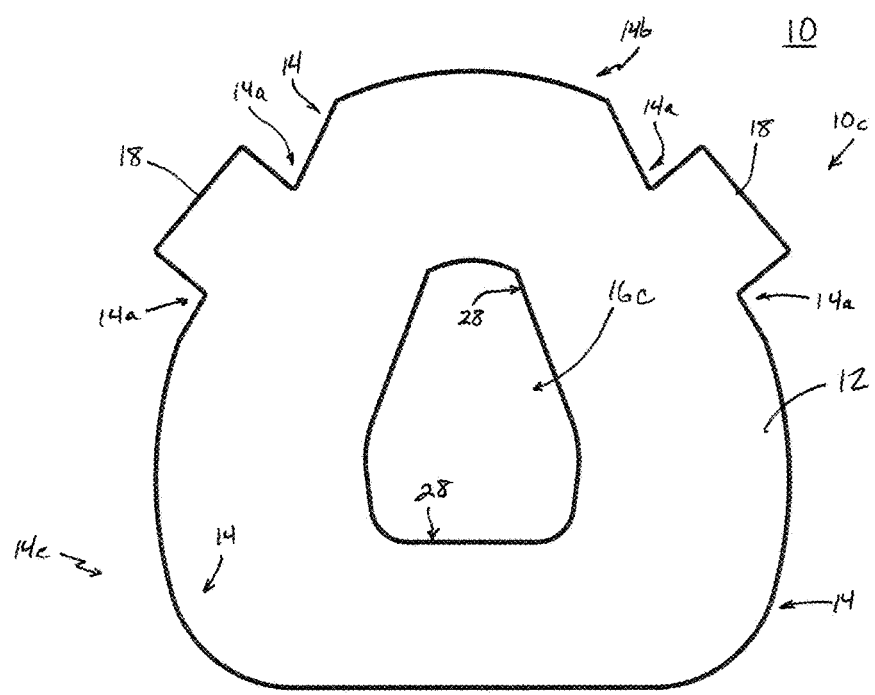
FIG. 3 is a top plan view of another respirator mask liner in accordance with the present invention.
Figure 4:
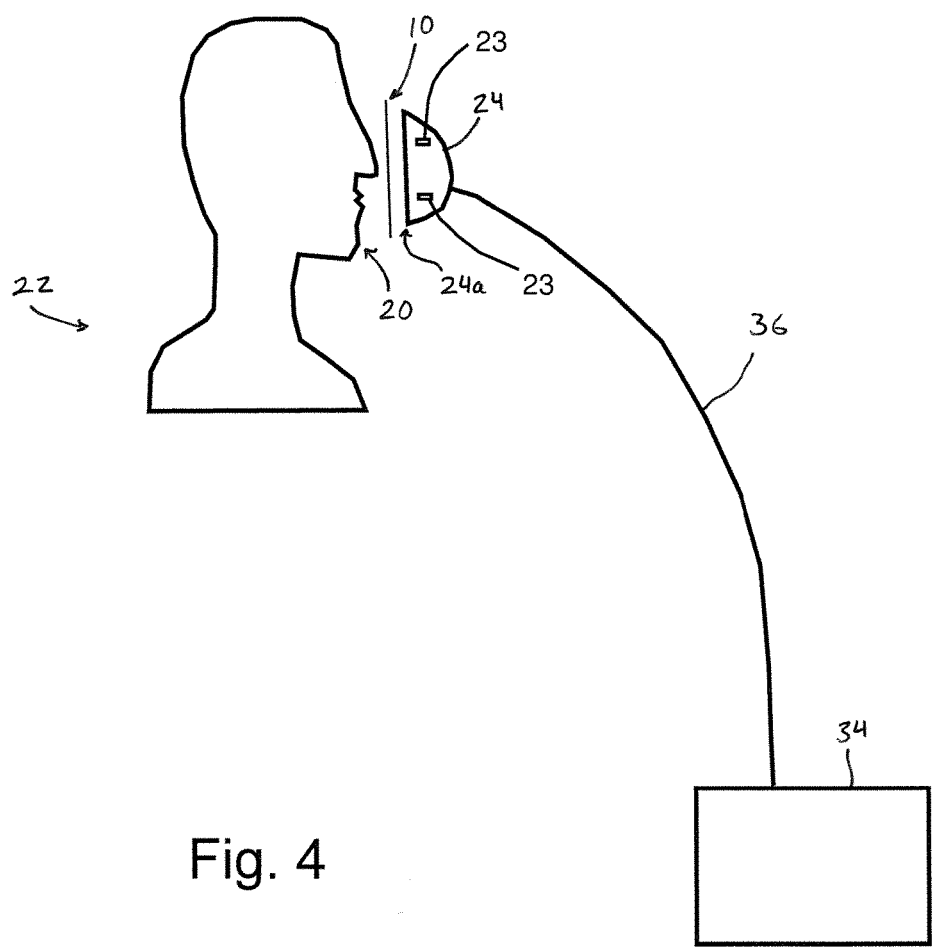
FIG. 4 is a partially exploded diagrammatic view of a respiration machine, gas line, respirator mask, mask liner, and head and upper torso of a human wearer.

In the illustrated embodiments of FIGS. 1-3, tabs 18 are generally rectangular in shape, although it will be appreciated that other shapes such as partial-circles or ovals, triangles, or other polygons may be used, without departing from the spirit and scope of the present invention. In the illustrated embodiment, tabs 18 are formed unitarily with perimeter edge portion 14 of flexible sheet 12, so that sheet 12 and tabs 18 are formed as a one-piece unit. However, it is envisioned that the tabs may be separate components that are attached to the flexible sheet during manufacture. Typically, at least two tabs 18 are provided along perimeter edge portion 14, such as shown in FIGS. 1-3. However, as few as one tab, or as many as four or more tabs (such as shown in FIGS. 1, 2 and 2C) may be provided. The tabs 18 are typically spaced apart from one another, and may be arranged in pairs, such as upper and lower pairs (FIGS. 1, 2 and 2C) or as just one pair (as in the upper pair shown in FIG. 3).

The size, shape and location of each tab 18, as well as the overall size and shape of each sheet 12, may be selected according to the particular respirator mask or masks for which a given mask liner 10 is intended. For example, different respirator masks may be sized and shaped to fit newborn infants, children or small adults, and large adults, and it is envisioned that mask liners 10 would be similarly sized according to the intended application. Tabs 18 may be positioned for ease of grasping by a wearer (such as between the thumb and forefinger) when liner 10 and a mask 24 are positioned on the wearer. For example, when four tabs 18 are provided, such as on the liners 10*a*, 10*b* of FIGS. 1 and 2, the wearer may (i) grasp one or both upper tabs to pull the liner upwardly, (ii) grasp one or both lower tabs to pull the liner downwardly, (iii) grasp one or both left-side tabs (including one upper tab and one lower tab) to pull the liner to the left, and (iv) grasp one or both right-side tabs (including one upper tab and one lower tab) to pull the liner to the right. Different pairs of tabs may also be simultaneously grasped and pulled in opposing directions, such as to flatten or remove any wrinkles that may have formed in the sheet 12 during positioning.

Tabs 18 may also be positioned according to the locations of tab-receiving or tab-engaging portions along the respirator mask, so that tabs 18 may cooperate with the mask to provide a visual indication of the proper alignment of the mask liner 10 along the mask. The mask itself may include tab-receiving portions such as flexible retainer clips, snaps, portions of a hook-and-loop fastener arrangement, clamping portions 23, or other mechanical fasteners or fastener portions that engage the tabs themselves, or that engage an attachment element disposed or positioned along the tab. For example, one or more tabs 18 of a given mask liner 10 may include an attachment element in the form of an adhesive, a portion of a hook-and-loop fastener, a magnet, a snap button portion, a hook that engages a hook-receiving portion along the mask, a loop of material such as elastic or string that engages a hook on the mask, or the like.

The attachment element engages or is received by a corresponding portion or surface of the respirator mask, such as a flat surface to which adhesive is readily securable, a corresponding portion of the hook-and-loop fastener, another magnet or magnetic surface, a corresponding snap button portion, etc. Optionally, some of the tabs 18 may include attachment elements as described above, while other tabs may not include any attachment elements at all, so that they remain available for grasping by the wearer. As a further option, a light pressure-sensitive adhesive may be applied to one surface of the mask liner, to facilitate releasably securing it to the gasket portion of the respirator mask, for example. For packaging and shipping, the adhesive may be covered by a non-stick adhesive backer material, which can be peeled away from the adhesive just prior to use.

Because respirator masks may be sized and shaped to accommodate just portions of the wearer's nose, or portions of both the nose and mouth, mask liners 10 may be sized and shaped accordingly. For example, the mask liner 10*c* of FIG. 3 has a hole 16*c* that is generally triangular in shape for accommodating portions of the wearer's nose. The mask liners 10*a*, 10*b* of FIGS. 1 and 2 have larger holes 16*a*, 16*b* that are sized and shaped to accommodate portions of the wearer's nose and mouth together. Holes 16*a*, 16*b* have tapered upper portions that may be similar in shape to the hole 16*c* of mask liner 10*c*, but with additional squared or enlarged bottom portions to also accommodate the wearer's mouth.

The dimensions and shape of perimeter edge portions 14 are also intended to closely conform to the shape of the gasket portion of a given respirator mask, to limit or prevent visual obstruction by the mask liner, while maintaining a sufficient seal if the wearer moves his or her mouth or jaw, such as while yawning. An upper region 14*b* of perimeter edge portion 14 is generally tapered to conform to the nose region of the wearer and reduce the likelihood that the mask liner will create a visual obstruction to the wearer, while a lower region 14*c* of perimeter edge portion 14 is generally wider to conform to the mouth region of the wearer.

Figure 2A:
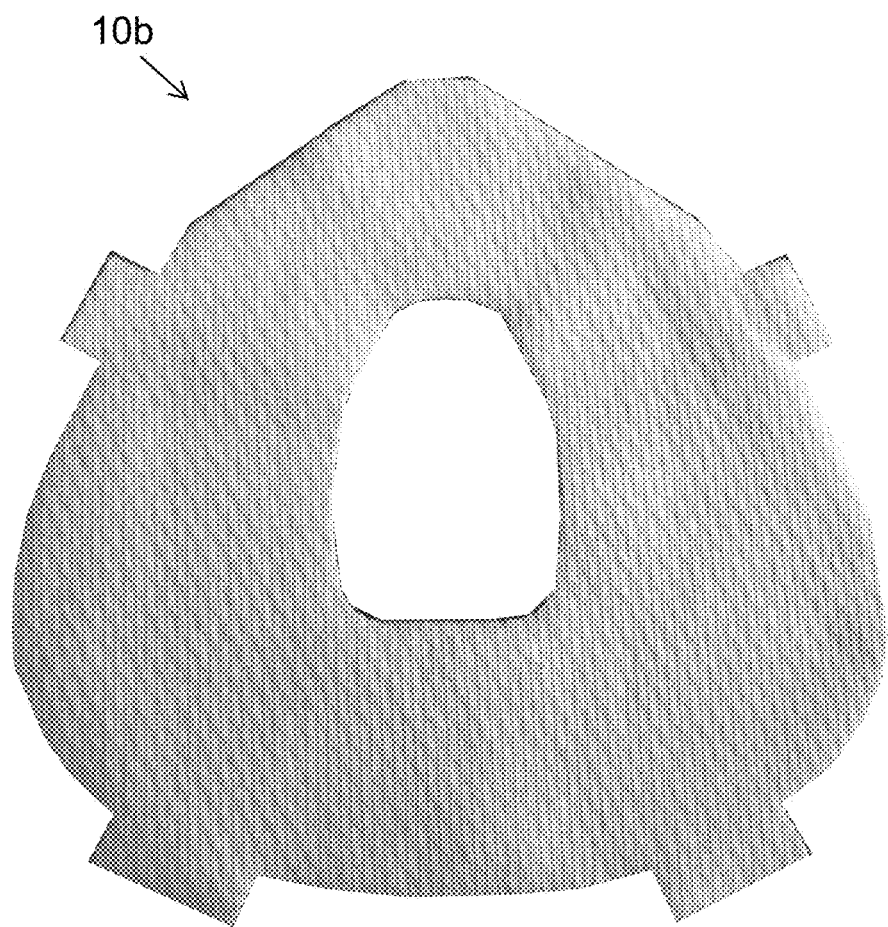
FIG. 2A is a top plan view of the respirator mask liner of FIG. 2, showing a surface texture and weave of the fabric.
Figure 5A:
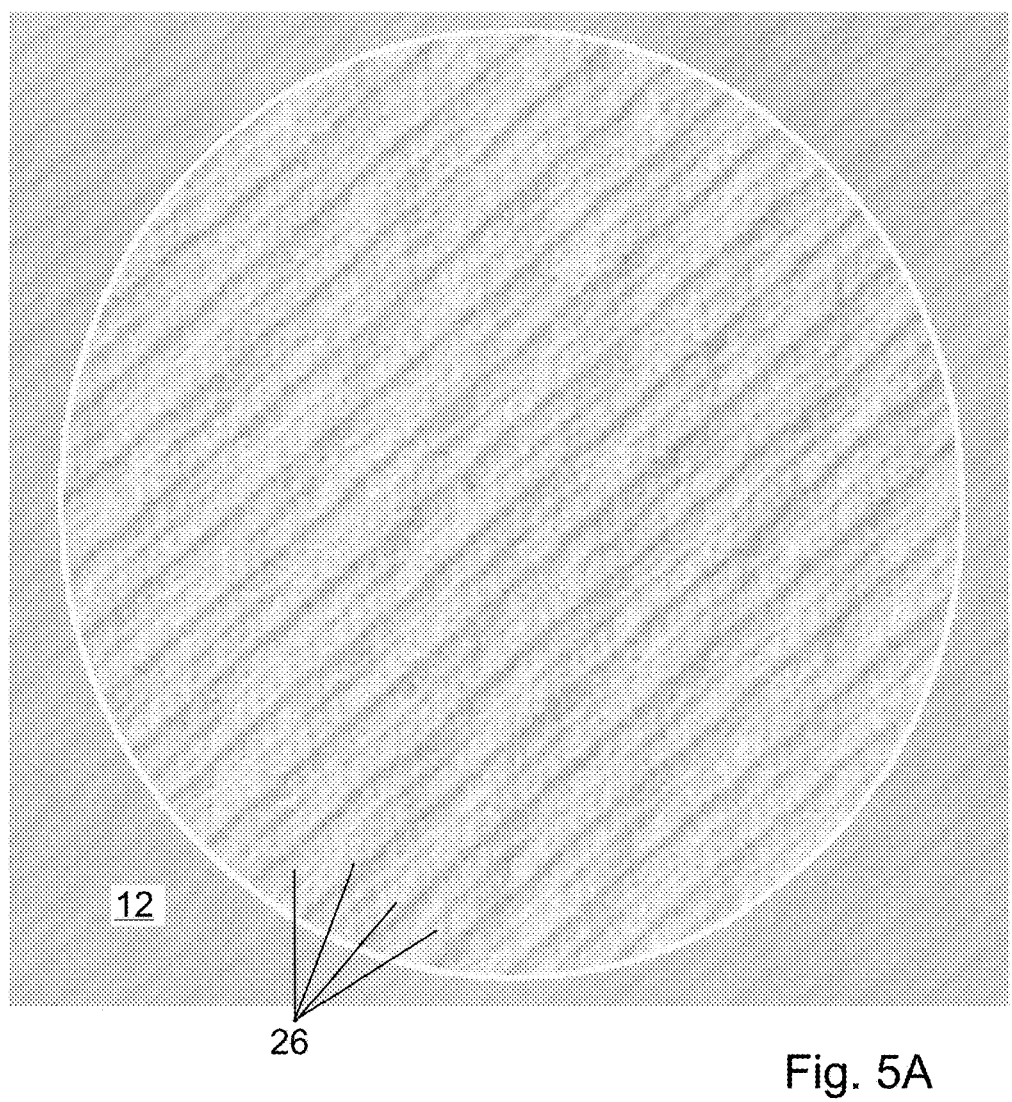
FIG. 5A is an enlarged view of a portion of a respirator mask liner, showing the surface texture thereof.
Figure 5B:
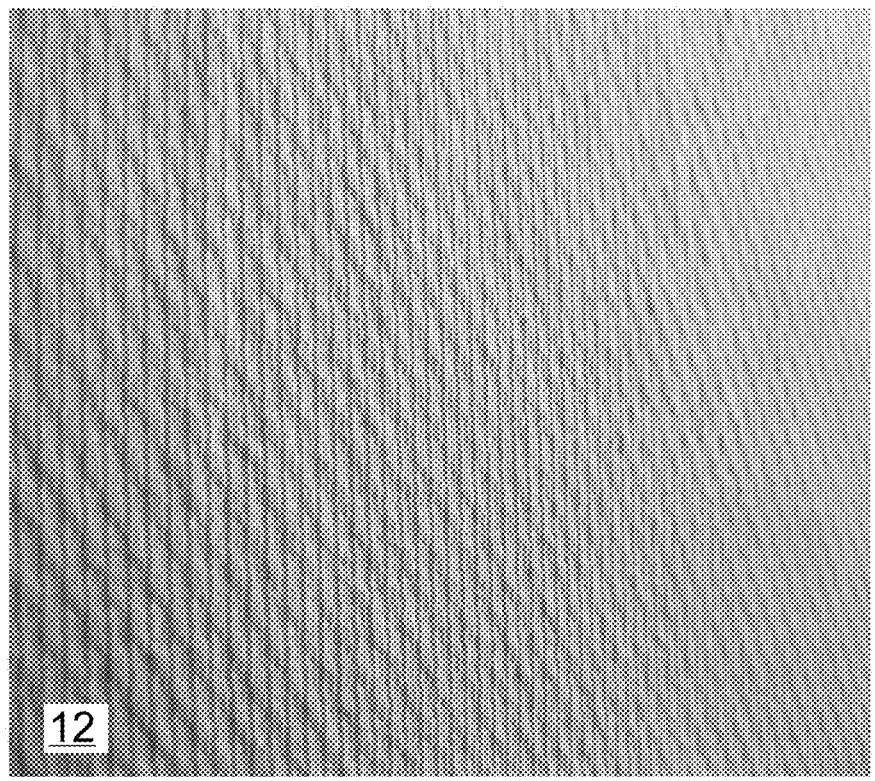
FIG. 5B is a top perspective view of a fabric section used in the production of respirator mask liners, showing the surface texture thereof.
Figure 5C:
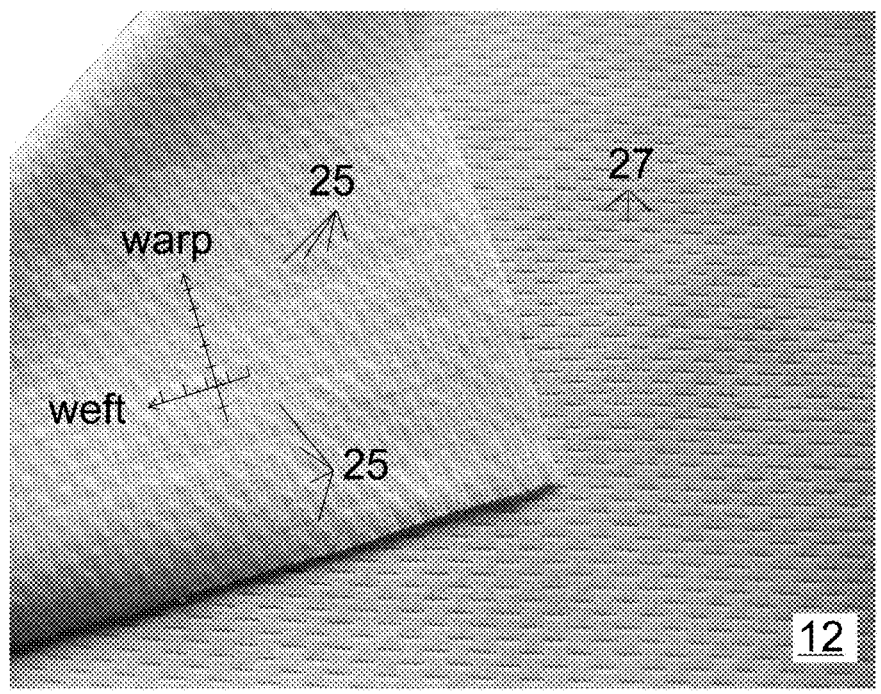
FIG. 5C is a top plan view of a folded corner region of the fabric section of FIG. 5B, in which a front surface is shown at left and a rear surface is shown at right.

The material of flexible sheet 12 provides cushioning and may enhance the seal between the wearer's face and the respirator mask. Flexible sheet 12 may be of moderate weight, such as about 6.7 oz/yd$^2$ (about 227 g/m$^2$), and may have a thickness of about 0.032 inches (about 0.8 mm), although it is envisioned that a wide range of weights and/or thicknesses could also provide satisfactory results. Optionally, and as shown in FIG. 5A, flexible sheet 12 is made of a woven fabric material having a microscopic ribbed pattern, with individual ribs 26 and cross-hatching forming a pattern of small pillow-like raised undulations acting as baffles or barriers to undesirable flow of air or other breathing gases between the respirator mask and the wearer's face during use. Optionally, and for example, the pillow-like raised undulations 25 may be spaced at intervals of one "pillow" 25 approximately every 2-3 mm in the weft direction, and at intervals of one approximately every 5-7 mm in the warp direction, or vice versa. The ribbed and cross-hatched pattern or surface texture may be imparted to the fabric, at least in part, by including elastic fibers in the warp threads that are woven during manufacturing using a jacquard loom attachment on a circular knitting machine, for example. The "pillow-like" surface texture, which is found primarily along a front surface that contacts a wearer's face, is readily visible with reference to FIGS. 2A, 5B, and 5C. A rear surface, which is shown at right in FIG. 5C, has a smoother contact surface with a pattern of small recess lines 27 where a high percentage of elastic fibers are located.

Flexible sheet 12 may be a woven fabric made from a blend of natural fibers (such as cotton) and synthetic fibers, such as polyester or elastane (e.g. "spandex") fibers that allow for enhanced stretch of the resulting fabric. For example, a blend of about 95 to 97 percent cotton and about 3 to 5 percent spandex, by weight, has been found to provide suitable results, although it is envisioned that a wide range of natural and synthetic fiber blends, or pure natural fiber, or pure synthetic fiber, may be used without departing from the spirit and scope of the present invention. For example, other desirable material properties may include moisture-wicking, absorbency and resistance to mold or other microbial or bacterial growth. Optionally, anti-bacterial or anti-microbial properties may be enhanced by the addition of a coating that is applied to the flexible sheet as in a spray or bath, or by infusing anti-bacterial or anti-microbial material into the fibers during manufacture of the fabric material. It is also envisioned that non-fabric materials may be used, such as flexible foam or foam-like material, paper or cellulose-based materials, or the like.

The material of flexible sheet 12 is sufficiently flexible to readily conform to the wearer's face and the gasket portion of the respirator mask, but is preferably not so thin and flexible as to be susceptible to curling at the edges due to handling or repeated use. It is also envisioned that the properties of the fabric sheet may be such that it will tend to maintain a given shape once it has assumed that shape during use, for example. Flexible sheet 12 may be die-cut or laser-cut from a sufficiently large sheet of material, such as woven fabric material having a composition as described above. If flexible sheet 12 is die-cut, it may be beneficial to heat-seal at least an inner edge 28 that defines hole 16, to partially melt loose fibers along the inner edge, thereby limiting or preventing fraying or unraveling of the fabric in that region. It is envisioned that laser cutting generally exhibits sufficient heat so that loose fibers are at least partially melted during the laser-cutting process, without need for additional heat-sealing.

Optionally, heat sealing of loose fibers along a cut edge may be accomplished via a heat sealing tool having a heated mandrel or shaft portion with a cross-sectional shape generally conforming to the shape of hole 16. It is further envisioned that a cutting die may be heated to provide the cutting and heat-sealing function essentially in a single step, such as using a heated steel rule die or the like. The mandrel, die, or other heat-sealing tool or element is heated to a temperature sufficient to at least partially melt at least some of the fibers of flexible sheet 12 at inner edge 28. For example, when flexible sheet 12 is made up of a blend of natural and synthetic fibers, with the synthetic fibers having a melting temperature that is lower than the burning or melting temperature of the natural fibers, the synthetic fibers may be readily melted with the heated mandrel, so that the melted portions of the synthetic fibers bond with the natural fibers to help ensure that none of the fibers at inner edge 28 are prone to fraying or separation. It will be appreciated that the outer perimeter edge portion 14 may be heat-sealed in a similar manner, which would be expected to improve the durability of the mask liner, particularly if it is being re-used and/or washed for re-use. In addition, the propensity for the material of flexible sheet 12 to be heat-sealed may be adjusted by changing the blend of the material, such as by changing the type of synthetic fiber or the ratio of synthetic fiber to natural fiber.

Referring again to FIG. 4, respirator mask 24 may be coupled to a positive-pressure breathing apparatus, such as a Constant Positive Airway Pressure (CPAP) machine 34, via a flexible hose 36 or the like. However, it is envisioned that mask liners 10 may be used with substantially any form of respirator mask, such as masks associated with pressurized air tanks or tanks containing other breathable gases, or other equipment capable of supplying air or breathable gases to a respirator mask. Such tanks and/or respirator systems may include firefighting equipment, oxygen systems or anesthetic delivery systems for medical or dental use, etc. Similar respirator masks are used for air filtration, such as at work sites where airborne particulates or harmful gases are present, and it is envisioned that the mask liners of the present invention may be used in substantially any of these or similar applications.

Therefore, the present invention provides a mask liner that enhances the comfort of wearing a respirator mask, particularly when the mask is worn for long periods, such as during sleep or for medical reasons. The mask liner is easy to use and adjust or position as needed, and may be reusable and even washable. The liner may also improve sealing between the wearer's face and the respirator mask, which may allow for reduced mask pressure without compromising performance. Moisture-wicking and pressure-reducing qualities can also reduce skin irritation and temporary pressure marks left in the skin upon removal of the mask and liner.

Changes and modifications to the specifically described embodiments may be carried out without departing from the principles of the present invention, which is intended to be limited only by the scope of the appended claims, as interpreted by the principles of patent law including the doctrine of equivalents.

The embodiments of the invention in which an exclusive property is claimed are defined as follows:

1. A respirator mask liner for engaging the face of a wearer, said mask liner comprising:
   a woven flexible sheet material having an outer perimeter edge portion and defining a hole spaced inwardly from said outer perimeter edge portion, the flexible sheet material including a plurality of tabs unitarily formed with said perimeter edge portion and
   projecting outwardly from respective portions of said perimeter edge portion that are adjacent said tabs, wherein said tabs comprise a pair of upper tabs arranged symmetrically at opposite sides of an upper portion of said flexible sheet material and a pair of lower tabs spaced from the pair of upper tabs and arranged symmetrically at opposite sides of a lower portion of said flexible sheet material; and
   an attachment element along a mask-facing surface of each of said tabs;
   wherein when said flexible sheet material is placed between the face of the wearer and a gasket portion of a respirator mask, each of said tabs projects outwardly beyond the gasket portion of the respirator mask, and wherein said attachment elements are configured to secure said flexible sheet portion to the respirator mask.

2. The respirator mask liner of claim 1, wherein each of said lower tabs is spaced equidistant from a respective one of said upper tabs.

3. The respirator mask liner of claim 1, wherein said attachment element is configured to releasably secure said flexible sheet material to the respirator mask.

4. The respirator mask liner of claim 3, wherein said attachment element comprises at least one chosen from (i) an adhesive, (ii) a portion of a hook-and-loop fastener, (iii) a magnet, (iv) a snap button, (v) a strap, and (vi) a clip.

5. The respirator mask liner of claim 1, wherein each of said tabs is configured to be engaged and releasably secured by a clamping portion of the respirator mask.

6. The respirator mask liner of claim 1, wherein said flexible sheet material comprises a woven blend of cotton and synthetic material.

7. The respirator mask liner of claim 6, wherein said synthetic material comprises polyester or elastane fibers.

8. The respirator mask liner of claim 6, wherein said flexible sheet material comprises about 97 percent cotton, by weight.

9. The respirator mask liner of claim 1, wherein said flexible sheet material comprises woven fibers having a ribbed and undulating pattern configured to obstruct airflow across a surface thereof.

10. The respirator mask liner of claim 9, wherein said ribbed and undulating pattern comprises a pattern of raised undulations that are spaced apart at intervals of about 2 mm-3 mm in a first direction and about 5 mm-7 mm in a second direction that is substantially perpendicular to the first direction.

11. The respirator mask liner of claim 1, further in combination with the respirator mask.

12. The respirator mask liner of claim 11, wherein said respirator mask is associated with at least one chosen from (i) a filter-type respirator, and (ii) a positive-pressure breathing apparatus.

13. The respirator mask liner of claim 12, wherein said respirator mask is associated with a positive-pressure breathing apparatus in the form of a Constant Positive Airway Pressure (CPAP) machine.

14. A respirator mask liner comprising:
a flexible woven fabric sheet portion comprising a blend of a lower-elasticity first fiber blended with a higher-elasticity second fiber having higher elasticity than said first fiber, wherein said first fiber makes up about 95 to 98 percent of said mask liner by weight and said second fiber makes up about 2 to 5 percent of said mask liner by weight;
an opening defined along an interior region of said fabric sheet portion, wherein said opening is configured to receive a portion of a wearer's nose and/or mouth; and
said flexible woven sheet portion comprises a skin-contacting surface that is woven to have a ribbed surface including a predetermined pattern of raised undulations configured to be placed in contact with the face of the wearer and to obstruct airflow between said skin-contacting surface and the wearer's skin.

15. The respirator mask liner of claim 14, wherein said first fiber comprises cotton and said second fiber comprises a synthetic polyester or elastane fiber.

16. The respirator mask liner of claim 14, wherein said fabric sheet portion comprises a perimeter edge portion surrounding said opening, and at least two tabs projecting outwardly from respective portions of said perimeter edge portion.

17. A respirator mask liner comprising:
a flexible sheet portion having an outer perimeter region generally conforming to a shape of a respirator mask and having a perimeter edge, wherein said outer perimeter region defines an inner opening along an interior region of said sheet portion, wherein said inner opening is configured to receive a portion of a wearer's nose and/or mouth;
a plurality of tabs unitarily formed with said flexible sheet portion and projecting outwardly from respective portions of said perimeter edge portion that are adjacent said tabs, wherein said tabs comprise a pair of upper tabs arranged symmetrically at opposite sides of an upper portion of said flexible sheet material and a pair of lower tabs arranged symmetrically at opposite sides of a lower portion of said flexible sheet material;
wherein said flexible sheet portion comprises a skin-contacting surface that is woven to have a ribbed surface including a predetermined pattern of raised undulations configured to be placed in contact with the face of the wearer and to obstruct airflow between said skin-contacting surface and the wearer's skin, wherein said raised undulations are spaced apart at first spacing intervals in a first direction and spaced apart at second spacing intervals that are greater than said first spacing intervals in a second direction that is substantially perpendicular to the first direction;
an anti-microbial substance incorporated at said flexible sheet portion, whereby said flexible sheet portion with said anti-microbial substance substantially inhibits growth of bacteria or microbes on said mask liner; and
wherein said anti-microbial substance is incorporated at said flexible sheet portion by at least one chosen from: (i) anti-microbial spray application, (ii) anti-microbial bath dip, and (iii) incorporation of anti-microbial fibers woven into said flexible sheet portion.

18. The respirator mask liner of claim 17, where said spacing interval is about 2 mm-3 mm and said second spacing interval is about 5-7 mm.

19. The respirator mask liner of claim 17, wherein said flexible sheet portion comprises:
an adhesive attachment element at a mask-facing surface of each of said tabs, said adhesive attachment elements configured to releasably secure said flexible sheet portion to the respirator mask; and
a woven fabric comprising a blend of a lower-elasticity first fiber blended with a higher-elasticity second fiber having higher elasticity than said first fiber, wherein said first fiber makes up about 95 to 98 percent of said mask liner by weight and said second fiber makes up about 2 to 5 percent of said mask liner by weight.

* * * * *